US007588785B2

(12) United States Patent
Evans et al.

(10) Patent No.: US 7,588,785 B2
(45) Date of Patent: Sep. 15, 2009

(54) METHODS AND KITS FOR REDUCING CELLULAR DAMAGE, INHIBITING FREE RADICAL PRODUCTION AND SCAVENGING FREE RADICALS

(75) Inventors: Gregory S. Evans, Grand Rapids, MI (US); Gregory Grochoski, Ada, MI (US); Russell K. Randolph, Anaheim, CA (US); Lynne M. Connor, Grand Rapids, MI (US); John V. Scimeca, Kentwood, MI (US); Kevin W. Gellenbeck, Poway, CA (US); James R. Mayne, Lowell, MI (US); Haeri Roh-Schmidt, Stockton, CA (US); Thomas J. Slaga, San Antonio, TX (US); Margaret Hanausek-Walaszek, Helotes, TX (US); Zbigniew Walaszek, Helotes, TX (US)

(73) Assignee: Access Business Group International LLC, Ada, MI (US)

( * ) Notice: Subject to any disclaimer, the term of this patent is extended or adjusted under 35 U.S.C. 154(b) by 125 days.

(21) Appl. No.: 11/624,687

(22) Filed: Jan. 18, 2007

(65) Prior Publication Data

US 2007/0243270 A1 Oct. 18, 2007

Related U.S. Application Data

(63) Continuation-in-part of application No. 10/705,081, filed on Nov. 10, 2003, now abandoned, and a continuation-in-part of application No. PCT/US2004/037362, filed on Nov. 10, 2004.

(51) Int. Cl.
| | |
|---|---|
| *A61K 36/82* | (2006.01) |
| *A61K 36/736* | (2006.01) |
| *A61K 36/752* | (2006.01) |
| *A61K 36/906* | (2006.01) |
| *A61K 36/00* | (2006.01) |

(52) U.S. Cl. ..................... 424/729; 424/735; 424/736; 424/756; 424/725

(58) Field of Classification Search ....................... None
See application file for complete search history.

(56) References Cited

U.S. PATENT DOCUMENTS

| | | | |
|---|---|---|---|
| 4,758,572 A | 7/1988 | Spector et al. | |
| 4,826,830 A | 5/1989 | Han et al. | |
| 5,401,504 A | 3/1995 | Das et al. | |
| 5,654,312 A | 8/1997 | Andrulis, Jr. et al. | |
| 5,827,880 A | 10/1998 | Malfroy-Camine et al. | |
| 5,852,056 A | 12/1998 | Samid | |
| 5,898,037 A | 4/1999 | Marx | |
| 5,985,850 A | 11/1999 | Falk et al. | |
| 6,048,844 A | 4/2000 | Falk et al. | |
| 6,074,647 A * | 6/2000 | Zimmerman et al. | ........ 424/735 |
| 6,132,711 A | 10/2000 | Backhaus et al. | |
| 6,200,594 B1 | 3/2001 | Ernest et al. | |
| 6,333,057 B1 | 12/2001 | Crandall | |
| 6,465,440 B2 * | 10/2002 | von Borstel et al. | ........... 514/45 |
| 6,627,231 B2 | 9/2003 | Soldati | |
| 6,669,966 B1 | 12/2003 | Antelman | |
| 6,989,150 B1 | 1/2006 | Golz-Berner et al. | |
| 7,195,787 B1 * | 3/2007 | Pykett et al. | ................ 424/728 |
| 2002/0013263 A1 | 1/2002 | Hsia | |

FOREIGN PATENT DOCUMENTS

FR        2815829        5/2002

* cited by examiner

*Primary Examiner*—Christopher R Tate
*Assistant Examiner*—Randall Winston
(74) *Attorney, Agent, or Firm*—Brinks Hofer Gilson & Lione

(57) ABSTRACT

Methods of reducing cellular damage are described that include (a) administering to the mammal an oral dosage form comprising a therapeutically effective amount of a first antioxidant, and (b) administering to the mammal a topical dosage form comprising a therapeutically effective amount of a second antioxidant, wherein at least one of the first antioxidant and the second antioxidant comprises acerola concentrate. Methods of inhibiting free radical production, methods of scavenging free radicals, and kits for reducing cellular damage are also described.

14 Claims, 2 Drawing Sheets

US 7,588,785 B2

METHODS AND KITS FOR REDUCING CELLULAR DAMAGE, INHIBITING FREE RADICAL PRODUCTION AND SCAVENGING FREE RADICALS

This application is a continuation-in-part of and claims priority to U.S. patent application Ser. No. 10/705,081, filed Nov. 10, 2003 now abandoned and PCT Application No. WO2004US0037362, filed Nov. 10, 2004, which published in English on May 26, 2005 as PCT WO 2005/047548, the entire contents of which are hereby incorporated by reference.

BACKGROUND

The present invention relates to methods, materials and kits for reducing cellular damage in mammals and, more particularly, to methods and materials and kits for protecting against injurious environmental stresses and their damaging effects on DNA and cellular structure, function, and growth. Kits discussed herein comprise combinations of oral and topical dosage forms.

Free radicals, or reactive oxygen species ("ROS") and other oxidizing species ("OOS") are thought to contribute to the development and progression of a variety of diseases or other abnormal conditions of the human body, ranging from skin conditions to cancer and cardiovascular disease. Increasingly, free radicals and their metabolites are being implicated in tissue injuries that lead to the initiation and/or promotion of multistage carcinogenesis.

The ROS species include superoxide (O2-), hydrogen peroxide (H2O2), peroxy radicals (HO2 and RO2) alkyl peroxide (R2O2), hydroxyl radical (.OH), alkoxy radical (.OR), and singlet oxygen. The OOS species include hypohalous acids (HOX) (where X is chloride, bromide, iodide), Z-amines (where Z is either chlorinated or ammoniated amine containing compounds, nitric oxide (NO), ammonia, cyclooxygenase, phospholipase A2, phospholipase C and transition metals.

Each of the ROS, directly or acting as an intermediate, are thought to act on various parts of cells through the cell membrane to adversely impact the human body. In view of the suspected causative or contributory role played by free radicals and their metabolites in the development and growth of cancerous cells, antioxidants and free radical scavengers have emerged as potential prophylactics for the prevention of cancer.

For reasons including reduced cost, increased bioavailability, and potentially reduced toxicity, it would be generally preferable to employ antioxidants and free radical scavengers or inhibitors obtained from natural sources, as opposed to specialty chemicals prepared synthetically, as prophylactics in therapies aimed at preventing or inhibiting the growth of cancerous cells. In addition, it would be desirable to identify naturally occurring antioxidants and free radical scavengers or inhibitors that exhibit high efficacy and potency in inhibiting the growth of free radical species both topically (e.g., at a region of skin, such as a portion of the hands or face, routinely subjected to potentially carcinogenic environmental stimuli) as well as systemically (e.g., inside the body, such as in an internal organ).

SUMMARY

The scope of the present invention is defined solely by the appended claims, and is not affected to any degree by the statements within this summary. By way of introduction, a first method of reducing cellular damage in a mammal includes (a) administering to the mammal an oral dosage form comprising a therapeutically effective amount of a first antioxidant, and (b) administering to the mammal a topical dosage form comprising a therapeutically effective amount of a second antioxidant, wherein at least one of the first antioxidant and the second antioxidant comprises acerola concentrate. Desirably, either the oral dosage form or the topical dosage form is administered first to the mammal, with the second of the two dosage forms being administered at any time during the metabolism of the first dosage form.

A first method of inhibiting free radical production in a mammal includes (a) administering to the mammal an oral dosage form comprising a therapeutically effective amount of a first antioxidant, and (b) administering to the mammal a topical dosage form comprising a therapeutically effective amount of a second antioxidant, wherein at least one of the first antioxidant and the second antioxidant comprises Acerola concentrate.

A first method of scavenging free radicals in a mammal includes (a) administering to the mammal an oral dosage form comprising a therapeutically effective amount of a first antioxidant, and (b) administering to the mammal a topical dosage form comprising a therapeutically effective amount of a second antioxidant, wherein at least one of the first antioxidant and the second antioxidant comprises Acerola concentrate.

A first kit for reducing cellular damage in a mammal includes (a) an oral dosage form comprising a therapeutically effective amount of a first antioxidant, and (b) a topical dosage form comprising a therapeutically effective amount of a second antioxidant, wherein at least one of the first antioxidant and the second antioxidant comprises Acerola concentrate.

A second method of reducing cellular damage in a mammal includes (a) administering to the mammal an oral dosage form comprising a therapeutically effective amount of a first phytochemical, and (b) administering to the mammal a topical dosage form comprising a therapeutically effective amount of a second phytochemical, wherein at least one of the first phytochemical and the second phytochemical comprises Acerola concentrate. Desirably, either the oral dosage form or the topical dosage form is administered first to the mammal, with the second of the two dosage forms being administered at any time during the metabolism of the first dosage form.

A second method of inhibiting free radical production in a mammal includes (a) administering to the mammal an oral dosage form comprising a therapeutically effective amount of a first phytochemical, and (b) administering to the mammal a topical dosage form comprising a therapeutically effective amount of a second phytochemical, wherein at least one of the first phytochemical and the second phytochemical comprises Acerola concentrate.

A second method of scavenging free radicals in a mammal includes (a) administering to the mammal an oral dosage form comprising a therapeutically effective amount of a first phytochemical, and (b) administering to the mammal a topical dosage form comprising a therapeutically effective amount of a second phytochemical, wherein at least one of the first phytochemical and the second phytochemical comprises Acerola concentrate.

A second kit for reducing cellular damage in a mammal includes (a) an oral dosage form comprising a therapeutically effective amount of a first phytochemical, and (b) a topical dosage form comprising a therapeutically effective amount of a second phytochemical, wherein at least one of the first phytochemical and the second phytochemical comprises Acerola concentrate.

DETAILED DESCRIPTION

Figure 1:
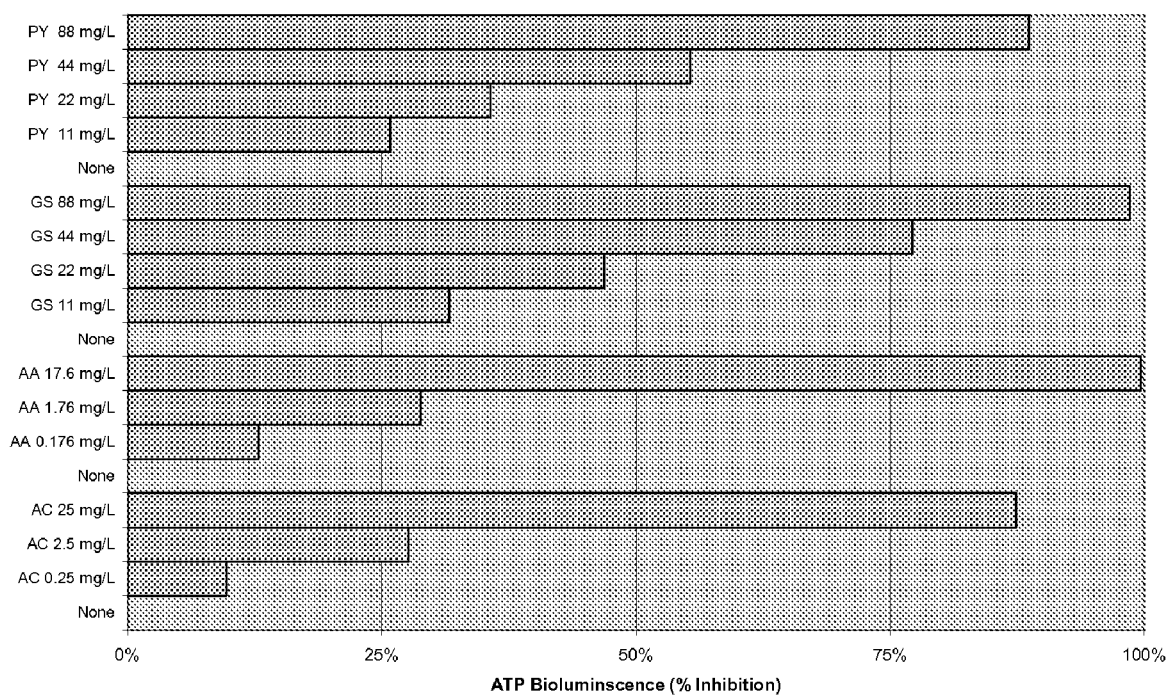
FIG. 1 shows a graph of dose response of 3PC cells to treatment with pycnogenol, grape seed extract, ascorbic acid, and Acerola concentrate.

It has been discovered that powerful antioxidant protection against injurious environmental stresses and their damaging effects on DNA and cellular structure, function and growth is provided by the administration of an oral dosage form containing a therapeutically effective amount of a first antioxidant and a topical dosage form containing a therapeutically effective amount of a second antioxidant, wherein at least one of the first antioxidant and the second antioxidant contains acerola concentrate. Moreover, it has been discovered that powerful antioxidant protection against injurious environmental stresses and their damaging effects on DNA and cellular structure, function and growth is likewise provided by the administration of an oral dosage form containing a therapeutically effective amount of a first phytochemical and a topical dosage form containing a therapeutically effective amount of a second phytochemical, wherein at least one of the first phytochemical and the second phytochemical contains acerola concentrate. For example, it has been discovered that a combination of oral and topical administration of antioxidants can provide significant protection against inflammatory and pigmentary alterations that are associated with damage to skin caused by ultra-violet (UV) radiation. Desirably, one or the other of the oral dosage form and the topical dosage form is administered first, with the second of the two dosage forms being administered at any time during the metabolism of the first dosage form.

Acerola, the ripe fruit of *Malpighia punicifolia* known as the Barbados cherry or the West-Indian cherry, is one of the very richest natural sources of ascorbic acid (i.e., Vitamin C). While the antioxidant activity of ascorbic acid to protect cells against damage from environmental stresses is documented, it has now been discovered in accordance with the present invention that the protective activity of acerola concentrate is, surprisingly and unexpectedly, more than four times higher than the activity one would expect based solely on ascorbic acid content. Methods and kits embodying features of the present invention are described hereinbelow.

Throughout this description and in the appended claims, the following definitions are to be understood. Terms that are not defined have the same meaning as commonly understood by one of ordinary skill in the art to which this invention belongs:

The phrase "reducing cellular damage" refers to one or more of (i) preventing damage to normal DNA or healthy cell structure, function or growth, (ii) partially or completely inhibiting further damage to DNA or unhealthy cell structure, function or growth, and (iii) reversing damage inflicted on previously healthy cells.

The phrases "inhibiting free radical production" and "scavenging free radicals" have the same meaning as commonly understood by one of ordinary skill in the art, namely where "inhibiting" generally refers to the inhibition of initiating events that occur in the free radical production pathway while "scavenging" refers to the inhibition of free radicals once they are produced. However, since there are situations where the production of one free radical creates another via a sequence of self-perpetuating chain reactions called "propagation", the phrase "inhibiting free radical production" applies to both inhibiting the initiating events and inhibiting free radicals that occur during propagation.

The phrases "acerola cherry concentrate" and "acerola concentrate" refer to either a liquid or solid concentrate of acerola fruit obtained by subjecting the naturally occurring fruit to a concentrative process, including but not limited to counter current extraction, ultrafiltration (UF), and the like.

The phrase "therapeutically effective amount" refers to an amount of an antioxidant or phytochemical, such as acerola concentrate that, when used in accordance with methods embodying features of the present invention, enables a target effect (e.g., preventing or reducing damage to DNA, cell structure, function, or growth, inhibiting free radical production, scavenging free radicals, etc.) to be achieved in a particular subject.

The term "metabolism" refers to every stage in the metabolic transformation of a dosage form, including the initial introduction of a dosage form into a subject (e.g., either by topical application, peroral consumption, or the like), the subsequent migration of one or more ingredients of the dosage form to a treatment site in or on the body, the consumption and/or degradation of one or more ingredients of the dosage form by the subject, and the eventual excretion of one or more ingredients of the dosage form and/or metabolites thereof.

The term "phytochemical" refers to any species produced by and/or obtained from a plant, including species that possess antioxidant properties.

A first series of representative methods of preventing or reducing cellular damage and/or inhibiting free radical production and/or scavenging free radicals in a mammal that embody features of the present invention, include (a) administering to the mammal an oral dosage form comprising a therapeutically effective amount of a first antioxidant, and (b) administering to the mammal a topical dosage form comprising a therapeutically effective amount of a second antioxidant, wherein at least one of the first antioxidant and the second antioxidant comprises acerola concentrate. Desirably, both the first antioxidant and the second antioxidant comprise acerola concentrate.

A second series of representative methods of reducing cellular damage and/or inhibiting free radical production and/or scavenging free radicals in a mammal that embody features of the present invention, include (a) administering to the mammal an oral dosage form comprising a therapeutically effective amount of a first phytochemical, and (b) administering to the mammal a topical dosage form comprising a therapeutically effective amount of a second phytochemical, wherein at least one of the first phytochemical and the second phytochemical comprises acerola concentrate. Desirably, both the first antioxidant and the second antioxidant comprise acerola concentrate.

Antioxidants suitable for use in accordance with the present invention may be derived from natural sources or prepared synthetically. Phytochemicals obtained from fruits and vegetables (e.g. polyphenols), particularly those with antioxidant properties, are especially desirable for use in accordance with the present invention. Suitable representative antioxidants and phytochemicals, in addition to acerola concentrate, include but are not limited to bioflavonoids, catechin-based preparations such as proanthanol and proanthocyanidin, grape seed extract, grape skin extract, pycnogenol, provatene, carotenoids such as β-carotene, sodium bisulfite, vitamins such as Vitamin E and Vitamin C (L-ascorbic acid), α-tocopherol, green tea extract, elderberry extract, rosemary extract, turmeric extract, bearberry (*Arctostaphylos Uva-Ursi*) extract, bitter orange peel extract, lemon extract, asparagus extract (stem or root), black cohosh (*Cimicifuga racemosa*) root extract, cucumber extract, quercetin, pine bark extract, α-lipoic acid, n-acetyl-L-cysteine, lutein, coenzyme Q10, complexes such as Complex 1, Complex 2, and Complex 3 shown in Table 1 below, and the like, and combinations thereof. Grape seed extract, pycnogenol, provatene, green tea extract, elderberry extract, lutein, coenzyme Q10, Complex 1, Complex 2, and Complex 3 are particularly desirable at present.

TABLE 1

| | Complex 1 | Complex 2 | Complex 3 |
|---|---|---|---|
| Tocopheryl Acetate | 25-75% | 25-75% | 25-75% |
| Tocopherol | 5-25% | 5-25% | 5-25% |
| Bioflavonoids | 1-10% | 1-10% | |
| Tetrahydrodiferuloylmethane (&) Tetrahydrodemethoxy-diferuloylmethane (&) Tetrahydrobisdemethoxy-diferuloylmethane | 1-10% | 1-10% | |
| Grape Seed Extract (&) Phospholipids | 5-25% | 1-10% | |
| Glutathione | 5-25% | 5-25% | 5-25% |
| Palmitoyl Hydroxypropyltrimonium Amylopectin/Glycerin Crosspolymer (&) Lecithin (&) *Camellia Sinensis* Extract | 5-25% | 5-25% | 5-25% |
| Superoxide Dismutase | 0.01-2% | 0.01-2% | 0.01-2% |
| Tetrahexyldecyl Ascorbate | | 10-30% | |
| Ubiquinone | | 1-10% | |
| Retinyl Acetate | | 1-10% | |
| Magnesium Ascorbyl Phosphate | | | 10-30% |
| Bitter Orange Peel Extract in Butylene Glycol | | | 0.01-2% |
| Cyclodextrin & Soybean (*Glycine Soja*) Germ Extract | | | 1-10% |
| Retinyl Palmitate | | | 1-10% |
| Licorice Extract | | | 0.01-2% |
| TOTAL | 100% | 100% | 100% |

The amounts shown in Table 1 represent percentage ranges of ingredients used to prepare each of Complexes 1, 2, and 3. The complexes shown in Table 1 are further defined in U.S. patent application Ser. No. 10/155,305, herein incorporated by reference.

Generally, the oral dosage form and the topical dosage form are administered to the mammal any time during the metabolism of the other dosage form. In other embodiments, the two administrations occur within a time frame of about 24 hours, 12 hours, 8 hours, 4 hours, 1 hour, 30 minutes, 15 minutes, 5 minutes, and 2 minutes. A substantially concomitant administration of the two dosage forms (i.e., the second dosage form is administered shortly after administration of the first dosage form, or in about 1 hour or less) is desirable at present.

All manner of oral dosage forms suitable for peroral administration of a pharmaceutical are contemplated for use in accordance with the present invention. Representative oral dosage forms for use in accordance with the present invention include but are not limited to pills, capsules, gelcaps, geltabs, beverages, chewing gums, chewable tablets, lozenges, viscous gels, troches, toothpastes, dental implants, gargling gels, mouth rinses, and the like, and combinations thereof. Presently preferred oral dosage forms include pills, capsules, gelcaps, geltabs, chewable tablets, lozenges, and troches.

In alternative embodiments in accordance with the present invention, the oral dosage form containing the first antioxidant is provided in the form of a controlled release delivery system of a type known in the art (e.g., see U.S. Pat. No. 6,004,582 to Faour et al.). The programmed release of the first antioxidant (e.g., acerola concentrate) into an individual's system may be desirable in order to minimize the number of oral dosage forms consumed by the individual in the course of a day (i.e., one controlled release dosage form may be ingested as opposed to multiple conventional dosage forms). Moreover, a controlled release delivery system used as an oral dosage form in accordance with the present invention, which contains acerola concentrate in its interior, may optionally be coated with an outer layer that likewise contains acerola concentrate, thus providing the rapid release of a bolus dose of acerola concentrate upon consumption.

All manner of topical dosage forms suitable for external application of a pharmaceutical are contemplated for use in accordance with the present invention. Representative topical dosage forms for use in accordance with the present invention include but are not limited to emulsions (e.g., creams, lotions, and the like), solutions, dispersions, gels, soaps, transdermal patches, and the like, and combinations thereof. Presently preferred topical dosage forms include emulsions, solutions, and gels.

The specific amounts of the first antioxidant and the second antioxidant in the oral dosage form and the topical dosage form, respectively, may vary with the subject, type of cells to be treated, format of dosage form, etc. For example, the weight, age, and overall health of a subject may be factors in determining what constitutes a therapeutically effective amount for the particular subject. Similarly, the physical properties of a dosage form (e.g., solid, liquid, concentrated, dilute, etc.) may be additional factors in determining a therapeutically effective amount. The therapeutically effective amounts of first and second antioxidants may be the same or different, and are preferably selected to provide optimum efficacy.

In presently preferred therapies embodying features of the present invention, both the first and second antioxidants comprise acerola concentrate. In presently preferred representative formulations of oral dosage forms for use in accordance with such therapies, the therapeutically effective amount of acerola concentrate is between about 50 mg and about 2000 mg, more preferably between about 350 mg and about 1500 mg, and still more preferably between about 400 mg and about 1200 mg. A particularly preferred oral dosage formulation at present is a tablet containing about 950 mg of acerola concentrate, which has an ascorbic acid content of about 120 mg or about 12.5% by weight. It is to be understood that the amount of acerola concentrate contained in an oral dosage form used in accordance with the present invention is dependent on the frequency of administration of the oral dosage form during the course of day. The presently preferred ranges described above correspond to a twice-daily peroral administration.

In other embodiments, an oral formulation of the present invention may comprise one or more of alpha-lipoic acid, N-acetyl-L-cysteine, rosemary extract, green tea extract, turmeric extract, quercetin, grape seed extract, grape skin extract, and pine bark extract. For example, an oral formulation of the present invention may comprise from approximately 5-25 mg of alpha-lipoic acid; approximately 150-250 mg of N-acetyl-L-cysteine; approximately 2-20 mg of rosemary extract; approximately 50-150 mg green tea extract; approximately 5-50 mg turmeric extract; approximately 5-50 mg quercetin; approximately 2-20 mg of grape seed extract; approximately 2-20 mg of grape skin extract; and approximately 2-20 mg of pine bark extract. In a more specific example, an oral formulation of the present invention may comprise approximately 15 mg of alpha-lipoic acid; approximately 200 mg of N-acetyl-L-cysteine; approximately 10 mg rosemary extract; approximately 100 mg green tea extract; approximately 25 mg turmeric extract; approximately 25 mg quercetin; approximately 10 mg grape seed extract; approximately 10 mg grape skin extract; and approximately 10 mg pine bark extract.

In presently preferred representative formulations of topical dosage forms in accordance with the above-described presently preferred therapies, the therapeutically effective amount of acerola concentrate is between about 15 mg and about 200 mg, more preferably between about 25 mg and about 100 mg, and still more preferably between about 50 mg and about 75 mg. A particularly preferred topical dosage formulation at present is a cream containing acerola concentrate in a concentration of about 5% by weight of the composition, such that an application of about 1.2 grams of cream provides about 65 mg of acerola concentrate. It is to be understood that the amount of acerola concentrate contained in a topical dosage form used in accordance with the present invention is dependent on the frequency of administration of the topical dosage form during the course of day and on the surface area of exposed skin that is to be covered. The presently preferred ranges described above correspond to a twice-daily topical administration to the hands and face of a subject.

In other embodiments, a topical formulation of the present invention may comprise one or more of Bearberry extract, bitter orange peel extract, lemon extract, cucumber extract, acerola concentrate, asparagus stem extract, asparagus root extract, and black cohosh extract. For example, a topical formulation of the present invention may comprise approximately 0.5-5% bearberry extract by weight of the total composition; approximately 0.025-0.5% bitter orange peel extract by weight of the total composition; approximately 0.025-0.5% lemon extract by weight of the total composition; approximately 0.025-0.5% cucumber extract by weight of the total composition; approximately 0.025-0.5% acerola concentration by weight of the total composition; approximately 0.25-2% asparagus stem extract by weight of the total composition; approximately 0.25-2% asparagus root extract by weight of the total composition; and approximately 0.25-2% black cohosh extract by weight of the total composition. In a more specific example, a topical formulation of the present invention may comprise approximately 2% bearberry extract by weight of the total composition; approximately 0.1% bitter orange peel extract by weight of the total composition; approximately 0.05% lemon extract by weight of the total composition; approximately 0.05% cucumber extract by weight of the total composition; approximately 0.1% acerola concentrate by weight of the total composition; approximately 0.5% asparagus stem extract by weight of the total composition; approximately 0.5% asparagus root extract by weight of the total composition; and approximately 0.5% black cohosh extract by weight of the total composition The frequency of repetition of methods embodying features of the present invention is not restricted, and corresponds to a therapeutically effective frequency. Presently preferred dosing frequencies include once-daily and twice-daily administrations of an oral dosage form and a topical dosage form.

The type of acerola concentrate used in accordance with the present invention is not limited. Concentrates of acerola fruit obtained via counter current extraction or an ultrafiltration (UF) method are preferred, with UF-prepared acerola concentrate being especially preferred at present. The acerola concentrate manufactured and sold by Nutrilite (Buena Park, Calif.) is a particularly preferred material for use in accordance with the present invention. Analysis of a representative sample of Nutrilite acerola concentrate indicates the presence of multiple flavonoids and the presence of ascorbic acid in a concentration of between about 14 and about 17 percent by weight.

Representative kits for reducing cellular damage and/or inhibiting free radical production and/or scavenging free radicals in a mammal that embody features of the present invention, include (a) an oral dosage form comprising a therapeutically effective amount of a first antioxidant, and (b) a topical dosage form comprising a therapeutically effective amount of a second antioxidant, wherein at least one of the first antioxidant and the second antioxidant comprises acerola concentrate.

Dosage forms embodying features of the present invention can be included in a kit, container, pack, or dispenser together with instructions for their use. The oral dosage form and topical dosage form may be provided in packaged combination in forms suitable for immediate application or in forms requiring modification prior to use. For example, a cream for use as a topical dosage form may be provided as a ready-to-use dermopharmaceutical containing a cream base in combination with a second antioxidant (e.g., acerola concentrate) or in two separate packages (e.g., cream base and acerola concentrate) which are to be combined and mixed prior to application. Packaging the ingredients of a dosage form in separate containers may permit long-term storage without substantially diminishing the functioning of the active components. Furthermore, ingredients can be packaged under inert environments (e.g., under a positive pressure of nitrogen gas, argon gas, or the like), which is especially preferred for ingredients that are sensitive to air and/or moisture.

Oral and topical dosage forms embodying features of the present invention can be supplied in all manner of containers such that the activities of the different components are substantially preserved, while the components themselves are not substantially adsorbed or altered by the materials of the container. Suitable containers include but are not limited to ampules, bottles, test tubes, vials, flasks, syringes, envelopes (e.g., foil-lined), and the like. The containers may be comprised of any suitable material including but not limited to glass, organic polymers (e.g., polycarbonate, polystyrene, polyethylene, etc.), ceramic, metal (e.g., aluminum), metal alloys (e.g., steel), cork, and the like. In addition, the containers may comprise one or more sterile access ports (e.g., for access via a needle), such as may be provided by a septum. Preferred materials for septa include rubber and polytetrafluoroethylene of the type sold under the trade name TEFLON by DuPont (Wilmington, Del.). In addition, the containers may comprise two or more compartments separated by partitions or membranes that can be removed to allow mixing of the components.

Kits embodying features of the present invention may also be supplied with instructional materials. Instructions may be printed (e.g., on paper) and/or supplied in an electronic-readable medium (e.g., floppy disc, CD-ROM, DVD-ROM, zip disc, videotape, audio tape, etc.). Alternatively, instructions may be provided by directing a user to an Internet web site (e.g., specified by the manufacturer or distributor of the kit) and/or via electronic mail.

In another embodiment of this invention, various methods are provided directed to reducing damage cause by reactive oxidative species. In one embodiment, the method involves administering to a mammal an oral dosage form comprising a therapeutically effective amount of a first antioxidant and a topical dosage form comprising a therapeutically effective amount of a second antioxidant. In this method, at least one of the first antioxidant or the second antioxidant comprises acerola concentrate.

The following examples and comparative study of antioxidant activities illustrate features in accordance with the present invention, and are provided solely by way of illustration. They are not intended to limit the scope of the appended claims or their equivalents. As will be seen from the following examples, the use of both an oral and topical dosage form, one of which contains an effective amount of acerola concentrate is more effective at preventing experimental carcinogenesis than either the topical or oral form alone. In addition, the examples provided below will show that acerola concentrate is more effective at preventing experimental carcinogenesis than an equivalent amount of synthetic Vitamin C.

Experimental Overview

Research has increasingly established antioxidants as protective or preventative agents against reactive oxygen species' potential to damage to DNA, cell structure, function and growth (see Recent Results in Cancer Res. 1999, 151, 29; Adv. Exp. Med. Biol. 1995, 369, 167). The research undertaken in the present invention evaluated the ability of the above described antioxidants to protect DNA, cellular structure and function using in vitro and in vivo experimental models. Antioxidants were initially evaluated in vitro for their antioxidant properties in a variety of reactive oxygen species assay systems. Subsequent to identifying top performing antioxidants in vitro, antioxidants were evaluated in vivo for their effectiveness when administered orally alone, topically alone, and in combined oral and topical applications.

In Vitro Research

Antioxidants were subjected to various in vitro biochemical assays to assess their antioxidant capabilities against different reactive oxygen species. Inhibition of linoleic acid auto-oxidation was assayed to address protection against peroxyl radical (J. Org. Chem., 1993, 58, 3532); inhibition of cytochrome C reduction was assayed to address protection against superoxide anion (J. Clin. Invest., 1973, 52, 741). In addition, the properties of antioxidants to inhibit reactive oxygen species-stimulated growth of cells was evaluated using an ATP bioluminescence assay (J. Immunol. Meth., 1993, 160, 81).

The concentration-dependent reactive oxygen scavenging abilities of several natural source and synthetic antioxidants were assessed. The natural source antioxidants and other chemicals used in this study were obtained from the following sources (product names and/or identifying characteristics are included in parentheses): tocopheryl acetate (VITAMIN E, SYNTHETIC N.F.—1000 IU/g) from Hoffman-LaRoche, Inc. (Nutley, N.J.); tocopherol (COVI-OX T-50 NATURAL) from Cognis Corp, USA (Cincinnati, Ohio); bioflavonoids (LEMON BIOFLAVONOIDS) from Access Business Group LLC (Lakeview, Calif.); tetrahydrodiferuloylmethane (&) tetrahydrodemethoxydiferuloylmethane (&) tetrahydrobisdemethoxydiferuloylmethane (TETRAHYDROCURCUMINOIDS) from Sabinsa Corporation (Piscataway, N.J.); grape seed extract (&) phospholipids (LEUCOSELECT PHYTOSOME) from Indena S.p.A. (Milan, Italy); glutathione (GLUTHAM) from Silab (Saint Viance, France); palmitoyl hydroxypropyltrimonium amylopectin/glycerin crosspolymer (&) lecithin (&) camellia sinensis extract; green tea (GLYCOSPHERE—GREEN TEA DECAFFEINATED) from Kobo Products (East Brunswick, N.J.); superoxide dismutase (S.O.D.C.am) from Silab; tetrahexyldecyl ascorbate (BV-OSC) from Barnet (Englewood Cliffs, N.J.); ubiquinone (UBIDECARENONE) from Seltzer Chemicals, Inc. (Carlsbad, Calif.); retinyl acetate (VITAMIN A ACETATE 2.8 M IU/g USP) from BASF (Mount Olive, N.J.); magnesium ascorbyl phosphate (VC-PMG-U5) from Nikko Chemicals, Co. (Tokyo, Japan); bitter orange peel extract in butylene glycol (BITTER ORANGE EXTRACT) from Centerchem (Norwalk, Conn.); cyclodextrin & soybean (glycine soja) germ extract (ISOFLAVONE SG-10) from Barnet; retinyl palmitate (VITAMIN A PALMITATE, USP, FCC, TYPE P1) from Hoffman-LaRoche, Inc.; licorice extract (LICHALCONE LR-15) from Barnet; elderberry extract (13% anthocyanosides) from Access Business Group, LLC; pycnogenol from Natural Health Sciences (Hillside, N.J.); provatene from Provatene Partners; green tea extract (95% polyphenols) from TSI; lutein (10% esters, 5% lutein) from Cognis Corp, USA; acerola concentrate (15% ascorbic acid) from Access Business Group, LLC; and CoQ10 from Kyowa Hakko U.S.A., Inc. (Aliso Viejo, Calif.).

Tissue Culture

The macrophage cell lines J774A.1 and P388D1 were obtained from the American Type Culture Collection (ATCC, Rockville, Md.). The 3PC-cell line was obtained from the University of Texas M.D Anderson Cancer Center, Science Park-Research Division (Smithville, Tex.). The macrophage J774A.1 cells were maintained in Dulbecco's Modified Eagle's Medium (DMEM) with 10% fetal bovine serum (Cyclone, Logan, Utah). The $1 \times 10^6$ cells were grown to confluence in a 25-mL flask in a 5-mL DMEM medium at 37° C. The medium was supplemented with L-glutamine and penicillin/streptomycin purchased from Gibco Laboratories (Grand Island, N.Y.). Another line of macrophage cells, P338D1, was maintained in RPMI 1640 containing 10% fetal bovine serum (Cyclone, Logan, Utah). The $1 \times 10^6$ cells were grown to confluence in a 25-mL flask with a 5-mL RPMI 1640 medium at 37° C., containing L-glutamine, penicillin/streptomycin, sodium bicarbonate, HEPES, D-glucose, and sodium pyruvate, all of which were purchased from Gibco Laboratories (Grand Island, N.Y.). The basal 3PC keratinocytes were maintained in Eagle Minimum Essential Minimum (EMEM) containing no calcium and 8% fetal bovine serum (Cyclone, Logan, Utah), and were grown at 37° C. in a 5% $CO_2$ atmosphere. The cells ($1 \times 10^6$) were grown to confluence in a 12-mL flask in a 5-mL EMEM medium containing L-glutamine and penicillin/streptomycin (Gibco Laboratories Grand Island, N.Y.), ethanolamine, phosphoethanolamine, insulin, epidermal growth factor, and transferrin (Sigma Chemical Co, St Louis, Mo.). The cells were more than 90% viable as estimated by trypan blue exclusion.

Preparation of Solutions

A stock solution of 0.3 phosphate buffer (pH 7.4) was treated overnight with Chelex-100 at room temperature and stored in a plastic bottle for no more than 2 weeks. Stock solutions of SDS and HDTBr (both 0.12 M) were prepared and used within 2 weeks. A solution of 0.5 M ABAP was freshly made in 0.05 phosphate buffer (pH 7.4). Stock solutions of antioxidants, except for L-ascorbic acid, acerola concentrate, and the mixed carotenoids, were freshly prepared in 0.05 phosphate buffer (pH 7.4) as 5 mg/mL stock solutions. The two water-soluble antioxidants were freshly prepared 30 min before use.

Linoleic Acid Auto-oxidation

The ability of peroxides to form free radicals and, consequently, to initiate lipid peroxidation and DNA damage may be measured by a simple, rapid, and convenient spectrophotometric technique, as described by W. A. Pryor et al. (*J. Org. Chem.*, 1993, 58, 3532). The method utilizes linoleic acid as an auto-oxidizable substrate, and monitors the appearance of linoleic acid hydroperoxide, which has an absorption at 233 nm. The method of forming radicals from peroxides in water employs a solution of 2.6 mM linoleic acid in 0.12 M SDS micelles in a 0.05 M phosphate buffer at pH 7.4. This solution is prepared and thermostated in a spectrophotometric cuvette. The initiator ABAP is then added in the presence or absence of various phytochemicals, and the rate of development of absorbance at 233 nm is followed.

Cytochrome C Reduction Assay

Superoxide anion production by macrophages was measured by the cytochrome C reduction assay described by B. M. Babior et al. (*J. Clin. Invest.*, 1973, 52, 741). The reaction mixture contained 1 mL of macrophages ($3\times10^6$ cell/mL) and 0.05 mM cytochrome C. The reaction mixture was incubated for 15 min at 37° C. The reactions were terminated by placing the tubes on ice. The mixtures were centrifuged at 1,500 g for 10 min at 4° C., and the supernatant fractions were transferred to clean tubes for subsequent spectrophotometric measurements at 550 nm. Absorbance values were converted into nanomoles of cytochrome C reduced by using the extinction coefficient of $2.1\times10^4$ M/cm/15 min.

ATP-Bioluminescence Assay

Many methods have been used for ATP determination, but the most widely used at present, in large part due to its sensitivity, is the luciferin-luciferase bioluminescent assay (see *J. Immunol. Meth.*, 1993, 160, 81). ATP bioluminescence has been used for determining levels of ATP in a number of different cell types. $MgATP^2$ converts the luciferin into a form capable of being catalytically oxidized by the luciferase in a high quantum yield chemiluminescent reaction. Under optimum conditions and at low ATP concentration, light intensity is linearly related to ATP concentration. Most ATP is found within living cells and links catabolic and anabolic processes. Cell injury or oxygen/substrate depletion results in a rapid decrease of the cytoplasmic ATP. Cellular ATP can be measured by direct lysis of the cells with a suitable detergent. The released ATP is then free to react with the luciferin-luciferase leading to light emission. The ATPLite-M system (Packard Instrument Co., Meriden, Conn.) is an adenosine triphosphate (ATP) monitoring system based on firefly luciferase. The ATPLite-M assay system is based on the production of light caused by the reaction of ATP with added luciferase and D-luciferin.

The abilities of the natural source antioxidants to scavenge oxygen free radicals was assessed using one or more in vitro assays, including but not limited to: linoleic acid autoxidation, cytochrome c reduction, and ATP-bioluminescence. Concentration-dependent responses for each antioxidant in each of the assays were utilized to estimate 50% effective inhibitory concentrations for each antioxidant (IC50; mg/L).

Table 2 below summarizes estimated IC50 values for selected top performing antioxidants as evaluated in the linoleic acid auto-oxidation and cytochrome c reduction assays. Note that the antioxidants shown in Table 2 are rank ordered in terms of increasing IC50, they were not statistically different from each other, i.e., they performed similarly well.

TABLE 2

Estimated IC50 Values of Selected Top Performing Natural Antioxidants (mg/L)

| Linoleic Acid Auto-oxidation (peroxyl radical scavenging) | Cytochrome C Reduction (superoxide anion scavenging) |
|---|---|
| Grape Seed Extract 0.8 | Elderberry Extract 6 |
| Elderberry Extract 0.8 | Complex 1 12 |
| Pycnogenol 2.5 | Grape Seed Extract 14 |
| Green Tea Extract 2.7 | Green Tea Extract 25 |
| Complex 1 3.0 | Acerola Concentrate 38 |

Figure 2:
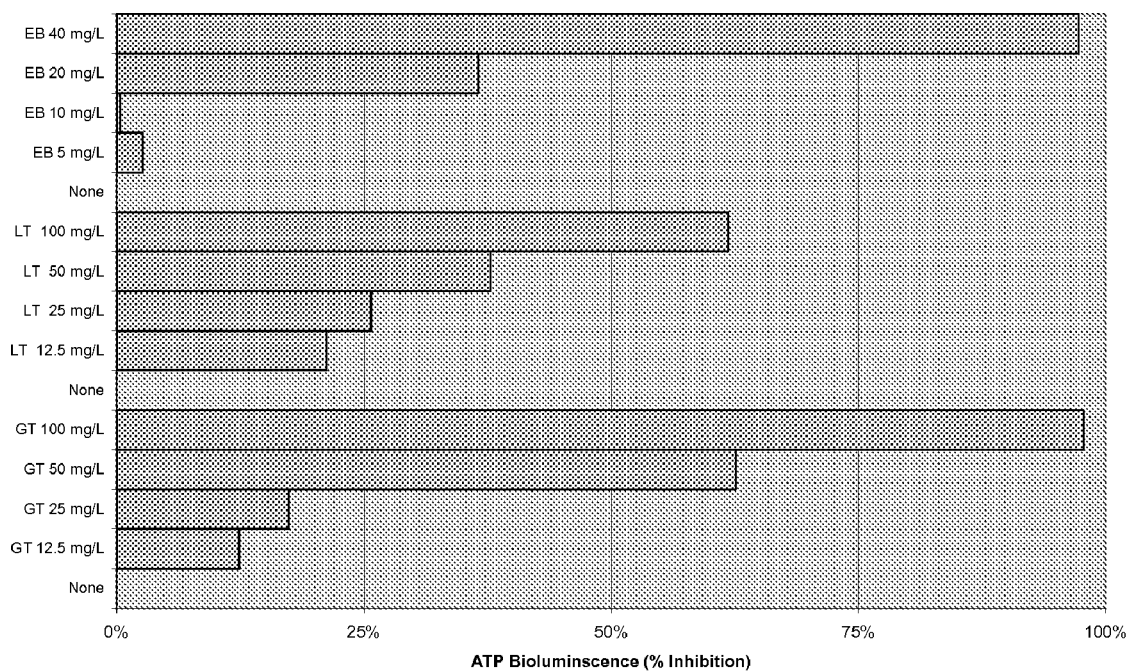
FIG. 2 shows a graph of dose response of 3PC cells to treatment with elderberry, lutein, and green tea extract.

The data shown in FIGS. 1 and 2 depict dose-response relationships for selected top performing antioxidants in the ATP-bioluminescence assay. The estimated IC50 values obtained from dose response relationships for these antioxidants are summarized in Table 3.

TABLE 3

| Antioxidant | Estimated IC50 (mg/L) in ATP Bioluminescence Assay |
|---|---|
| Lutein | 70.8 |
| Green Tea Extract | 43.0 |
| Pycnogenol | 35.8 |
| Elderberry Extract | 24.5 |
| Grape Seed Extract | 21.5 |
| Acerola Concentrate | 8.2 |
| Ascorbic Acid | 4.6 |

It is clear from the data shown in FIGS. 1 and 2 and Table 3 above that the natural source antioxidants examined in this study—particularly those containing a variety of different antioxidants, such as acerola concentrate—are effective inhibitors of oxygen free radical formation.

A comparison of the performance of acerola concentrate to that of ascorbic acid on a weight basis reveals that these two antioxidant materials possess similar antioxidant capacity. This result is surprising and unexpected as acerola concentrate contains about only 15% by weight as ascorbic acid. This strongly suggests that one or more compositional ingredients of acerola concentrate other than vitamin C (e.g., flavonoids) significantly enhances the effectiveness of endogenous vitamin C antioxidant potency. Calculation of IC50 values based upon ascorbic acid content reveals that acerola concentrate is approximately four times more potent than can be explained based solely on vitamin C content, as shown in Table 4 below.

TABLE 4

| Antioxidant | Estimated IC50 based on weight (mg/L) | Estimated IC50 Based on vitamin C content (mg/L) | Percent |
|---|---|---|---|
| Acerola Concentrate (AC) | 8.16 | 1.22 | 15% |
| Ascorbic Acid (AA) | 4.60 | 4.60 | 100% |

Ratio of Effectiveness AC:AA = 3.76

In Vivo Research Overview

One of the best studied in vivo models for evaluation of environmental stress response effects on DNA and cell damage is the mouse skin system in which the skin is treated with a chemical compound known to damage DNA and cell structure and function. Multiple topical applications of low dose dimethylbenzanthracene (DMBA) results in predictable irritation/inflammation in the skin which is accompanied by damage to DNA and normal cell structure, function and growth (Adv. Exp. Med. Biol. 1995, 369, 167). The aforementioned antioxidant compounds were evaluated for their ability to reduce or prevent this damage via oral or topical or combined oral plus topical application prior to or during DMBA treatment. Following dosing and treatment, skin DNA and cell structure and function were evaluated using three endpoints, epidermal hyperplasia, 8-OH-dG formation, and Ha-ras mutation. Each method is described briefly below.

Epidermal Hyperplasia Method

Seven week old, pathogen free, female SENCAR mice were purchased from the National Cancer Institute (NCI, Frederick, Md.). Mice were randomized by weight and separated into groups (n=5 mice per group). Experimental groups of mice were treated on shaved dorsal skin with antioxidants, 15 min prior to treatment with DMBA (25 µg per treatment). In topical experiments, different doses, i.e., 0.5, 1.0, 2.0, and/or 4.0 mg, of test or reference antioxidants per mouse were applied topically twice weekly for a total of 8 treatments (4 weeks). In each experiment, a positive control group was treated with DMBA only, no antioxidants were administered. Negative control groups were treated with vehicle (acetone) only. The DMBA solution was prepared in acetone immediately before use, under yellow light. Most antioxidants were administered in acetone. Antioxidants that were not soluble in acetone to the desired concentration, were dissolved in the necessary volume: mixture of acetone and water or ethanol. All topical treatments were administered in a final volume of 0.2 mL. Dietary antioxidants were administered in at least two different doses, i.e., 0.5%, 1.0% and/or 5.0%. Test and reference antioxidants were administered in AIN-93G based diets beginning 2 weeks prior to the first topical application of DMBA. DMBA was again administered a total of 8 times over 4 weeks with no other topical treatments. The same control groups were maintained. Both positive and negative control groups were fed a standard AIN-93G diet (i.e., not supplemented with antioxidants). Animals were sacrificed 48 hours after the final DMBA treatment. At sacrifice the shaved dorsal skin section was removed. A one square centimeter section was removed from the center of the skin, preserved in 10% buffered formalin, and embedded for histological preparation. Epidermal thickness was determined in each animal from at least 20 randomly selected sites per animal using formalin-fixed, paraffin-embedded 5 µm sections stained with hematoxylin and eosin. The remaining skin was frozen in liquid nitrogen. All frozen sections were stored at −70C until analysis for isolation of DNA.

8-OH-dG Formation Method

DNA was isolated from freshly-frozen tissues of 5 mice per group following non-phenol extraction and ethanol precipitation. Approximately 100 µg of isolated DNA was digested to nucleosides with nuclease P1 and alkaline phosphatase. Quantification of modified DNA bases was accomplished by high performance liquid chromatography (Shimadzu, Japan) with electrochemical detection unit (ECD) using an ESA system (ESA, Inc. Chelmsford, Mass.); normal bases (dG) were quantified by HPLC (78) using an UV detection system. Data were expressed as pmol 8-OH-dG/105 pmol dG. All analyses were performed in duplicate or triplicate, with appropriate standard curves to correlate area units or peak height with concentration. Skin from mice treated with DMBA (100 nmols, 2×/wk for 4 wks) served as the positive control and skin from solvent-treated and untreated animals served as negative controls.

Ha-ras Mutation Method

DNA isolated from freshly-frozen tissues of 5 mice per group was analyzed for mutations in codon 61 of c-Ha-ras by PCR analysis. The procedure used for Ha-ras codon 61 was derived from Nelson et al (Proc. Natl. Acad. Sci. USA 89, 6398). The 3MSP61 mutant reverse primer was designed so that its 3' end nucleotide (A) pairs with the middle nucleotide (underlined) of a CAA->CTA transversion in codon 61, and selectively amplifies mutated DNA under the conditions described below. The assay was based on the fact that Taq polymerase lacks 3' exonuclease activity and thus cannot repair a mismatch at the 3' end of the annealed primer. The conditions of the assay depend on the reverse primer failing to anneal sufficiently to the wild type sequence so that extension does not occur. Using the same forward primer, one reaction was run with the reverse mismatch primer (3MSP61mut) and another reaction was run with a reverse wild type primer (3MSP61 wt). This protocol detects only CAA->CTA transversion, mutations that are the most prevalent in codon 61 point mutations. The ratio of the amount of wild type DNA to mutated DNA was determined by quantifying intensity of 32P labeling on autoradiograms. The DNA from the plasmid pHras61mut was used as a positive control sample. The plasmid pHras61 contains cloned exon 2 Ha-ras DNA from a Sencar mouse tumor. The cloned mutation was verified by DNA sequencing. The mutation is the CAA->CTA transversion in codon 61 (located in exon 2) of the mouse Ha-ras gene.

In Vivo Results Summary

Acerola concentrate and selected other antioxidants exhibited potent antioxidant activity in the in vivo assays, whether administered topically, orally, or in combination. Significantly, Acerola concentrate was a component among the five top performing combination therapies, including a topical/oral combination consisting only of Acerola concentrate.

DMBA-induced Epidermal Hyperplasia

As shown below in Table 5, and similar to the results of the ATP Bioluminescence assay discussed above, acerola concentrate containing approximately 15% vitamin C tended to performed on par with pure ascorbic acid when applied topically or when consumed orally, both inhibiting DMBA-induced epidermal hyperplasia 66% to 70%. These results for either dosage route are a manifestation of the synergism between the ascorbic acid and, presumably, other flavonoids contained in acerola concentrate.

Surprisingly, combination oral and topical acerola concentrate delivered more antioxidant protection than either dosage form alone (see combination treatment in Table 5). When equivalent doses are administered as a combination of oral and topical dosing, DMBA-induced epidermal hyperplasia was essentially 100% inhibited, i.e., epidermal cells were apparently completely protected from the damaging insult of DMBA treatment.

TABLE 5

Inhibition of DMBA-Induced Epidermal Hyperplasia

| Topical application | Inhibition (%) |
|---|---|
| Ascorbic Acid (0.5 mg) | 66% |
| Ascorbic Acid (2.0 mg) | 66% |
| Acerola Concentrate (0.5 mg) | 68% |

TABLE 5-continued

Inhibition of DMBA-Induced Epidermal Hyperplasia

| Topical application | Inhibition (%) |
|---|---|
| Acerola Concentrate (1.0 mg) | 80% |
| Acerola Concentrate (2.0 mg) | 70% |
| Dietary | |
| Ascorbic Acid (1.0%) | 83% |
| Ascorbic Acid (5.0%) | 86% |
| Acerola Concentrate (1.0%) | 70% |
| Acerola Concentrate (5.0%) | 82% |
| Combination topical and oral | |
| Acerola Concentrate diet alone (0.5%) | 73% |
| Acerola Concentrate (0.5%) + Acerola Concentrate (1.0 mg) | 98% |
| Acerola Concentrate(0.5%) + Acerola Concentrate(2.0 mg) | 105% |
| Acerola Concentrate diet alone (1.0%) | 81% |
| Acerola Concentrate (1.0%) + Acerola Concentrate (1.0 mg) | 96% |
| Acerola Concentrate (1.0%) + Acerola Concentrate (2.0 mg) | 96% |

Thus, an enhancement in epidermal hyperplasia inhibiting activity of acerola concentrate is observed when a first therapeutically effective amount is administered in an oral dosage form and a second therapeutically effective amount is administered in a topical dosage form, in accordance with the present invention. Moreover, there is additional enhancement in the antioxidant activity of acerola concentrate when it is administered in combination with other antioxidants orally and/or topically. Representative synergistic combinations of antioxidants in accordance with the present invention include but are not limited to a mixture of acerola concentrate, vitamin E, and Complex 2, and a mixture of acerola concentrate, vitamin E, and Complex 1.

As shown in Table 6, combination application of oral and topical acerola concentrate surprisingly exhibits synergistic antioxidant protection against DMBA-induced formation of 8-OH-dG, a marker of genetic damage. When acerola concentrate is administered either orally or topically alone, there is 15% to 30% inhibition of 8-OH-dG formation in vivo in response to DMBA. When the same doses of acerola concentrate is administered both orally and topically, there is 81% inhibition of 8-OH-dG formation, more than twice the inhibition observed with each dosage form alone, a clear demonstration of synergistic protection against 8-OH-dG formation by oral and topical acerola concentrate.

TABLE 6

Inhibition of DMBA-induced 8-OH-dG formation

| 8-OH-dG formation | % Inhibition |
|---|---|
| Acerola Concentrate 2.0 mg (topical alone) | −30.8 |
| Acerola Concentrate 1% (dietary alone) | −15.1 |
| Acerola Concentrate (1% dietary) + Acerola Concentrate (2 mg topical) | −81.5 |

As shown in Table 7, topical acerola concentrate surprisingly exhibits almost complete antioxidant protection against DMBA-induced formation Ha-ras formation, another marker of genetic damage.

TABLE 7

Inhibition of DMBA-induced Ha-ras mutation

| Topical | Ha-ras Formation |
|---|---|
| DMBA (pos. control) | 18.39 |
| Acetone (neg. control) | 3.05 |
| Acerola Concentrate (4 mg) + DMBA | 3.73 |
| Ascorbic Acid (4 mg) + DMBA | 6.19 |

In Vivo Human Study

Study Design

Two groups, (Group I, n=10 and Group II, n=15) of female subjects between the ages of 22 and 61 were inducted into this study. The subjects were Caucasian, Hispanic, or Asian. The subjects were required to abstain from using any skin lightening treatment and to avoid direct daily sun exposure on the lower back for at least seven days prior to the study commencement and during the course of the study. The study lasted 10 weeks. Study participants were limited to subjects with Fitzpatricks skin type II. This skin type is described in the Federal Register, volume 64, No. 98 at page 27690 (1999) as follows: Type II—always burns easily; tans minimally. This characterization is based on the first 45 to 60 minutes of sun exposure after a winter season of no sun exposure.

In both Groups, study participants did not have uneven skin tones, pigmentation, scars or other irregularities. Potential participants were excluded if they had a history of any form of skin cancer, melanoma, lupus, psoriasis, connective tissue disease, diabetes, or if the potential participant was photosensitive. In addition, potential participants were excluded if taking high levels of antioxidants, birth control, hormone replacement therapy, anticancer drugs, antidepressants, antihistamines, antimicrobials, antiparasitic, antipsychotic, diuretics, hypoglycemics, non-steroidal anti-inflammatory drugs or aspirin.

Each study participant in Groups I and II provided six test sights. Test sites were located on the lower untanned region of the back to the right and left of the midline. Each test site was comprised of a 50 cm² box, with three test sites on each side of the back (for a total of six test sites). Test sites were delineated as 50 cm² boxes using a gentian violet surgical marker. Two of the sites (referenced as "site 1" and "site 2") were irradiated with twice the Minimal Erythema Dose ("MED") exposure times and two sites (referenced as "site 3" and "site 4") were irradiated with twice the Minimal Persistent Pigmentation Dose ("MPPD") exposure times. MED and MPPD exposure times were calculated as described below under the headings "MED Determination" and "MPPD Determination." The last two test sites (referenced as "site 5" and "site 6") were left non-irradiated. The test sites for groups I and II are explained more fully below in Tables 8 and 9.

TABLE 8

Group I test sites

| GROUP I TEST SITES LEFT OF BACK MIDLINE (ONLY ORAL FORMULATION ADMINISTERED) | GROUP I TEST SITES RIGHT OF BACK MIDLINE (ORAL AND TOPICAL FORMULATIONS ADMINISTERED) |
|---|---|
| Site 1—2 × MED untreated | Site 2—2 × MED + topical formulation |
| Site 3—2 × MPPD untreated | Site 4—2 × MPPD + topical formulation |

TABLE 8-continued

Group I test sites

| GROUP I TEST SITES LEFT OF BACK MIDLINE (ONLY ORAL FORMULATION ADMINISTERED) | GROUP I TEST SITES RIGHT OF BACK MIDLINE (ORAL AND TOPICAL FORMULATIONS ADMINISTERED) |
|---|---|
| Site 5—Non-irradiated | Site 6—Non-irradiated + topical formulation |

TABLE 9

Group II test sites

| GROUP II TEST SITES LEFT OF BACK MIDLINE (UNTREATED—NO FORMULATIONS ADMINISTERED) | GROUP II TEST SITES RIGHT OF BACK MIDLINE (ONLY TOPICAL FORMULATION ADMINISTERED) |
|---|---|
| Site 1—2 × MED untreated | Site 2—2 × MED + topical formulation |
| Site 3—2 × MPPD untreated | Site 4—2 × MPPD + topical formulation |
| Site 5—Non-irradiated | Site 6—Non-irradiated + topical formulation |

An artificial light source was used to calculate the MED and the MPPD. Specifically, a 150 watt Xenon Arc Solar Simulator (Solar Light Co., Philadelphia, Pa., Model 14S and 16S) with a continuous emission spectrum in the UVB range of 290 to 400 nm was used. Xenon arc is selected on the basis of its black body radiation temperature of 6000 K. This produces continuous UV spectra (all wavelengths) substantially equivalent to that of natural sunlight. See Berger, D. S., "Specification and Design of Solar Ultraviolet Simulators." *J. Invest. Dermatol.* 53:192-199, 1969, the entire contents of which are hereby incorporated by reference.

The solar simulator is equipped with a dichroic mirror (reflects all radiation below 400 nm) and which works in conjunction with a 1 mm thick Schott WG-320 filter (absorbs all radiation below 290 nm) to produce simulation of the solar UVA-UVB spectrum was used. A 1 mm thick UG 11 filter is attached to remove reflected (infra-red, greater than 700 nm) heat and remaining visible radiation. A 3 mm thick Schott WG-335 filter along with 1 mm thick Schott UG 11 was used to produce simulation of the solar UVA spectrum. UVA-UVB and UVA radiation will be monitored continuously during exposure using a Model DCS-1 Sunburn UV Meter/Dose Controller System (Solar Light Co.) formerly known as the Robertson-Berger Sunburn Meter (R-B meter). Measurements were taken at a position within 8 mm from the surface of the skin. The field of irradiation was 1 cm in diameter. The solar simulator warmed up for at least 15 minutes before use and the power supply output was recorded.

MED Determination

To determine a subject's MED, a minimum of five UV exposures with the Xenon Arc Solar Simulator artificial light source, calculated using a geometric progression of $1.25^n$, were administered within a site. An individual subject's MED is the shortest time of exposure that produces minimally perceptible erythema at 16 to 24 hours post irradiation. Lamp irradiance was monitored continuously throughout the duration of the UV exposures. Erythema on each test site was graded according to the following scale:

−=No Erythema

+/−=Questionable Erythema

+=Minimal Erythema

++=Slight Erythema

+++=Well-Defined Erythema

1=Erythema and Edema

2=Erythema and Edema in vesicles

MPPD Determination

The threshold dose for Persistent Pigmentation Dose ("PPD") on unprotected skin was determined by administering a series of exposures with Xenon Arc Solar Simulator in 25% dose increments of UVA radiation in geometric progression within a site. The MPPD is the smallest UVA dose required to produce PPD 2 to 4 hours after exposure. This procedure was modified where the MPPD was determined 16 to 24 hours after exposure. A minimum of 5 exposures was performed. The MPPD of unprotected skin was determined under standardized lighting. The threshold response was taken as an unequivocal pigment darkening with distinct borders. Persistent pigmentation on each sub site was graded according to the following scale:

−=No discernable pigment darkening

+/−=Barely perceptible pigment

+=Unequivocal pigment darkening, distinct borders, lasting more than 2 to 4 hours ++=Pronounced pigment darkening, lasting more than 2 to 4 hours MED and MPPD were determined by both using a Spectrophotometer and visual grading. Specifically, a Spectrophotometer CM-2600d was used. This instrument utilizes the D/8 geometry conforming to CIE No. 15, ISO 7724/1, ASTM E1164, DIN 5033 Tei17, and JIS Z8722-1982 (diffused illumination/8° viewing system) standards, and offers simultaneous SCI (specular component included) and SCE (specular component excluded) measurements. Light from the xenon lamps diffuse on the inner surface of the integrating sphere and illuminate the specimen uniformly. The light reflected by the specimen surface at an angle of 8 degrees normal to the surface is received by the specimen-measuring optical system. The diffused light in the integrating sphere is received by the illumination-monitoring optical system and guided to the sensor. The light reflected by the specimen surface and the diffused light are divided into each wavelength component by the specimen-measuring optical system and illumination-monitoring optical sensor, respectively, and then signal proportional to the light intensity of each component are output to the analog processing circuit. By using the outputs from the specimen-measuring optical system and the illumination-monitoring sensor for calculation, compensation for slight fluctuations in spectral characteristics and the intensity of the illumination light is performed (Double-beam system). The instrument then assigns a numerical value, L*, to the specimen. An increase in the L* value indicates lightening of the color and any decrease of the L* value is indicative of darkening of the color:

In addition to use of the Spectrophotometer, a trained technician visually graded or assessed product performance and evaluated the effect of the product (if any) on the skin. A scale of 0-10 was used where 0 represented light skin, 5 represented moderate coloring of the skin and 10 represented dark skin.

Test Method

During the 10 week test period, test sites on participants in Group I were analyzed on 11 separate occasions and test sites on participants in Group II were analyzed on 7 separate occasions.

Group I

For Group I, during week 1 of the test period, three separate analyses were conducted on consecutive days. At the first analysis, the MED and MPPD for each subject was determined and spectrophotometer readings were taken. At the second analysis, an evaluation and visual grading of MED and MPPD were carried out and the appropriate test sites were irradiated at 2×MED and 2×MPPD (See Tables 8 and 9 above for test sites). At the third analysis, visual grading of the 2×MED and 2×MPPD was conducted and spectrophotometer readings were taken.

The fourth analysis occurred during week 2 of the test period. During the fourth analysis MED and MPPD were again determined for each subject and spectrophotometer readings were taken. In addition, subjects were instructed to begin taking an oral supplement three times a day until the end of the 10 week test period. The oral supplement administered comprised the formulation shown below in Table 10.

TABLE 10

Oral Supplement Formulation

| Ingredient | Amount |
| --- | --- |
| Alpha-lipoic acid | 15 mg |
| N-acetyl-L-cysteine | 200 mg |
| Rosemary extract | 10 mg |
| Green tea extract | 100 mg |
| Turmeric extract | 25 mg |
| Quercetin | 25 mg |
| Grape seed extract | 10 mg |
| Grape skin extract | 10 mg |
| Pine bark extract | 10 mg |
| Magnesium stearate, vegetable | |
| Silicon dioxide, NF fine powder | |
| Starch, Corn, pregelatinized | |

No analyses were conducted on Group I during the weeks 3-5 of the test period. During week 6 of the test period, three separate analyses were conducted on Group I, again on consecutive days. Specifically, at the fifth analysis, MED and MPPD for each subject was determined and spectrophotometer readings were taken. At the sixth analysis, an evaluation and visual grading of MED and MPPD were carried out and the appropriate test sites were irradiated at 2×MED and 2×MPPD (See Tables 8 and 9 above for test sites). At the seventh analysis, visual grading of the 2×MED and 2×MPPD was conducted and spectrophotometer readings were taken. In addition, at the seventh analysis, Group I subjects were instructed to apply a provided topical formulation twice a day using two pumps of the product (35-40 mg) per application until the end of the 10 week test period. Topical applications were to be made according to the test sites as outlined above in Tables 8 and 9. The topical formulation that was administered is shown below in Table 11:

TABLE 11

Topical Formulation

| Ingredient | Percentage of the total composition |
| --- | --- |
| Carbomer 940 | 0.250% |
| Acrylates/C10-30 alkylacrylates crosspolymer | 0.150% |
| Disodium EDTA | 0.200% |
| Methylparaben | 0.200% |
| Propylparaben | 0.070% |
| Ethoxydiglycol | 3.000% |
| Tetrahexadecyl ascorbate | 0.750% |
| Butylene glycol | 5.000% |
| Sodium hydroxide (50% solution) | 0.370% |
| Bearberry extract | 2.000% |
| Benzyl alcohol | 1.000% |
| Bitter orange peel extract | 0.100% |
| Lemon extract and Cucumber extract | 0.100% |
| Acerola concentrate | 0.100% |
| Asparagus stem extract | 0.500% |
| Asparagus root extract | 0.500% |
| Black cohosh extract | 0.500% |

An eighth analysis of Group I was conducted during week 7. A ninth analysis of Group I was conducted during week 8. A tenth analysis of Group I was conducted during week 9. The eleventh and final analysis of Group I was conducted during week 10. At each of these analyses, both visual grading and spectrophotometer readings were recorded for each test site.

Group II

For Group II, no analyses were conducted until week 6 of the 10 week test period. During week 6 three separate analyses of each participate in Group II were conducted on consecutive days. At the first analysis, the MED and MPPD for each subject was determined and spectrophotometer readings were taken. At the second analysis, an evaluation and visual grading of MED and MPPD were carried out and the appropriate test sites were irradiated at 2×MED and 2×MPPD (See Tables 8 and 9 above for test sites). At the third analysis, visual grading of the 2×MED and 2×MPPD was conducted and spectrophotometer readings were taken. In addition, at the third analysis during week 6, Group II subjects were instructed to apply a provided topical formulation twice a day using two pumps of the product (35-40 mg) per application until the end of the 10 week test period. Topical applications were to be made according to the test sites as outlined above in Tables 8 and 9. The topical formulation that was administered is shown above in Table 11.

A fourth analysis of Group II was conducted during week 7. A fifth analysis of Group II was conducted during week 8. A sixth analysis of Group II was conducted during week 9. The seventh and final analysis of Group II was conducted during week 10. At each of these analyses, both visual grading and spectrophotometer readings were recorded for each test site.

Results

The results are reported below in Tables 12-17. As indicated above, an increase in the L values listed below indicates lightening of skin color and any decrease of the L value is indicative of darkening of skin color. These results demonstrate that the oral formulation of the present invention tested in this study exhibited the ability to provide resistance to pigment darkening. These results further demonstrate that the topical formulation of the present invention tested in this study exhibited the ability to lighten skin pigment and/or prevent darkening. For example, Table 15 illustrates an increase in L values for subjects administered only the oral formulation and a greater increase in subjects administered both the oral and topical formulations.

TABLE 12

Group I: Spectrophotometer Readings, Mean Difference from Baseline

| Analysis number | ORAL FORMULATION ADMINISTERED | | ORAL AND TOPICAL FORMULATIONS ADMINISTERED | |
|---|---|---|---|---|
| | SCI | SCE | SCI | SCE |
| | 2 × MED—L values | | 2 × MED—L values | |
| 7  | −4.20% | −4.40% | −2.56% | −2.63% |
| 8  | −8.19% | −8.41% | −9.95% | −10.10% |
| 9  | −7.09% | −7.41% | −5.92% | −6.22% |
| 10 | −4.41% | −5.53% | −3.60% | −3.89% |
| 11 | −3.47% | −4.19% | −1.64% | −1.73% |
| | 2 × MPPD—L values | | 2 × MPPD—L values | |
| 7  | −3.82% | −4.10% | −1.84% | −2.01% |
| 8  | −5.18% | −5.45% | −4.38% | −4.56% |
| 9  | −4.52% | −4.82% | −4.19% | −4.40% |
| 10 | −3.86% | −4.20% | −3.78% | −4.00% |
| 11 | −2.89% | −3.27% | −1.61% | −1.86% |
| | Non-Irradiated—L values | | Non-Irradiated—L values | |
| 7  | −1.21% | −1.27% | −0.95% | 0.05% |
| 8  | 0.66%  | 0.52%  | 1.16%  | 1.56% |
| 9  | 1.74%  | 1.57%  | 1.94%  | 2.35% |
| 10 | 1.02%  | 0.80%  | 1.69%  | 2.01% |
| 11 | 1.58%  | 1.32%  | 0.71%  | 0.97% |

TABLE 13

Group II: Spectrophotometer Readings, Mean Difference from Baseline

| Analysis number | NO FORMULATIONS ADMINISTERED— UNTREATED | | ONLY TOPICAL FORMULATION ADMINISTERED | |
|---|---|---|---|---|
| | SCI | SCE | SCI | SCE |
| | 2 × MED—L values | | 2 × MED—L values | |
| 3 | −5.79% | −5.79% | −5.75% | −5.84% |
| 4 | −8.40% | −7.43% | −7.43% | −7.59% |
| 5 | −2.96% | −3.15% | −3.23% | −3.56% |
| 6 | −0.69% | −0.72% | 0.28%  | 0.06%  |
| 7 | −0.44% | −0.83% | 0.24%  | 0.20%  |
| | 2 × MPPD—L values | | 2 × MPPD—L values | |
| 3 | −4.00% | −4.06% | −3.63% | −3.64% |
| 4 | −3.91% | −4.05% | −4.20% | −4.37% |
| 5 | −2.19% | −2.37% | −1.73% | −1.95% |
| 6 | −0.78% | −0.98% | 0.14%  | 0.06%  |
| 7 | −0.62% | 0.55%  | −0.09% | −0.23% |
| | Non-Irradiated—L values | | Non-Irradiated—L values | |
| 3 | −0.59% | −0.55% | −0.19% | −0.24% |
| 4 | 0.46%  | 0.34%  | 1.28%  | 1.13%  |
| 5 | 0.97%  | 0.81%  | 1.96%  | 1.77%  |
| 6 | 1.06%  | 0.92%  | 2.45%  | 2.27%  |
| 7 | 0.85%  | 0.67%  | 2.28%  | 2.18%  |

TABLE 14

Visual Evaluation, Mean Difference from Baseline

| | ONLY ORAL (Group I) | ONLY TOPICAL (Group II) | ORAL and TOPICAL (Group I) | UNTREATED— NO FORMULATION ADMINISTERED (Group II) |
|---|---|---|---|---|
| 2 × MED | A#* 8 = −5.00%    | A# 4 = −19.33% | A# 8 = −19.00%  | A# 4 = −16.00% |
|         | A# 9 = −25.00%    | A# 5 = −37.33% | A# 9 = −35.00%  | A# 5 = −36.00% |
|         | A# 10 = −44.00%   | A# 6 = −66.67% | A# 10 = −43.00% | A# 6 = −64.00% |
|         | A# 11 = −59.00%   | A# 7 = −76.00% | A# 11 = −61.00% | A# 7 = −70.00% |
| 2 × MPPD | A# 8 = −21.00%   | A# 4 = −15.33% | A# 8 = −16.00%  | A# 4 = −20.00% |
|         | A# 9 = −44.00%    | A# 5 = −39.33% | A# 9 = −41.00%  | A# 5 = −44.67% |
|         | A# 10 = −60.00%   | A# 6 = −70.00% | A# 10 = −54.00% | A# 6 = −64.67% |
|         | A# 11 = −69.00%   | A# 7 = −77.33% | A# 11 = −65.00% | A# 7 = −79.33% |

*A# = analysis number

TABLE 15

Mean Difference of Spectrophotometer Readings at Analyses 2 and 3 versus Analyses 6 and 7

|  | ONLY ORAL FORMULATION | | ORAL and TOPICAL FORUMLATIONS | |
| --- | --- | --- | --- | --- |
|  | Analyses 2 & 3 | Analyses 6 & 7 | Analyses 2 & 3 | Analyses 6 & 7 |
| 2 × MED (a values) | | | | |
| SCI | −208.97 | 75.92 | −208.97 | −175.77 |
| SCE | −227.27 | 305.78 | −227.27 | −205.87 |
| 2 × MPPD (L values) | | | | |
| SCI | −7.06 | −3.79 | −7.06 | −1.75 |
| SCE | −6.67 | −4.06 | −6.67 | −1.93 |

TABLE 16

Conversion of 2 × MED to J/m$^2$ (oral formulation) GROUP I

| Subject No. | Analysis 2 2 × MED | Analysis 6 2 × MED | Analysis 2 J/m$^2$ | Analysis 6 J/m$^2$ |
| --- | --- | --- | --- | --- |
| I-1 | 98 | 122 | 743.12 | 925.11 |
| I-2 | 98 | 122 | 743.12 | 925.11 |
| I-3 | 122 | 122 | 925.11 | 925.11 |
| I-4 | 78 | 78 | 591.47 | 591.47 |
| I-5 | 78 | 122 | 591.47 | 925.11 |
| I-6 | 78 | 98 | 591.47 | 743.12 |
| I-7 | 98* | DC* | 743.12* | DC* |
| I-8 | 98 | 122 | 743.12 | 925.11 |
| I-9 | 62 | 122 | 470.14 | 925.11 |
| I-10 | 62 | 98 | 470.14 | 743.12 |
| I-11 | 98 | 122 | 743.12 | 925.11 |
| Mean | 87.20 | 112.80 | 661.23 | 855.35 |
| % Difference |  | 29.36 |  | 29.36 |
| one-tailed P distribution |  | 0.000803 |  | 0.000803 |
| % Confidence Level |  | 99.92 |  | 99.92 |
| Statistical Significance |  | Significant |  | Significant |
| two-tailed P distribution |  | 0.001607 |  | 0.001607 |
| % Confidence Level |  | 99.84 |  | 99.84 |
| Statistical Significance |  | Significant |  | Significant |

TABLE 17

Conversion of 2 × MPPD to J/m$^2$ (oral formulation) GROUP I

| Subject No. | Analysis 2 2 × MPPD | Analysis 6 2 × MPPD | Analysis 2 J/m$^2$ | Analysis 6 J/m$^2$ |
| --- | --- | --- | --- | --- |
| I-1 | 390 | 488 | 261300 | 326960 |
| I-2 | 488 | 488 | 326960 | 326960 |
| I-3 | 488 | 488 | 326960 | 326960 |
| I-4 | 488 | 488 | 326960 | 326960 |
| I-5 | 390 | 488 | 261300 | 326960 |
| I-6 | 312 | 488 | 209040 | 326960 |
| I-7 | 312* | DC* | 209040* | DC* |
| I-8 | 390 | 488 | 261300 | 326960 |
| I-9 | 488 | 488 | 326960 | 326960 |
| I-10 | 488 | 488 | 326960 | 326960 |
| I-11 | 390 | 488 | 261300 | 326960 |
| Mean | 431 | 488 | 288904 | 326960 |
| % Difference |  | 13.17 |  | 13.17 |
| one-tailed P distribution |  | 0.010416 |  | 0.010416 |
| % Confidence Level |  | 98.96 |  | 98.96 |
| Statistical Significance |  | Significant |  | Significant |
| two-tailed P distribution |  | 0.020833 |  | 0.020833 |
| % Confidence Level |  | 97.92 |  | 97.92 |
| Statistical Significance |  | Significant |  | Significant |

Tables 16 and 17 may be used along with the data presented in Tables 12-15 to demonstrate that the oral and topical formulations of the present invention cause an increase in the mean energy required to induce a 2×MED response and the dose of ultraviolet light required to illicit a 2×MPPD response.

Specifically, following the procedures outlined above, 10 subjects were administered an oral formulation comprising 15 mg alpha lipoic acid, 200 mg N-acetyl cysteine, 100 mg green tea extract, 25 mg turmeric extract and 25 mg quercetin three times a day for 28 consecutive days. As outlined above, skin located on the sun-protected lower back of each subject was UV-irradiated. Skin reddening or darkening were quantified using a spectrophotometer as discussed above and reported in Tables 12-15. After 28 days of taking the oral formulation described above, the mean energy required to induce a 2×MED response increased by 29% from 661 J/m$^2$ to 855 J/m$^2$ (p<0.001). Furthermore, oral supplementation raised the dose of UVA required to illicit 2×MPPD 13% from 289 kJ/m$^2$ to 327 kJ/m$^2$ (p<0.001). Thus, this data illustrates that formulations of the present invention, which comprise antioxidants, provide significant protection against inflammatory and pigmentary alterations that are associated with damage to skin caused by ultraviolet irradiation.

The foregoing detailed description and examples have been provided by way of explanation and illustration, and are not intended to limit the scope of the appended claims. Many variations in the presently preferred embodiments illustrated herein will be obvious to one of ordinary skill in the art, and remain within the scope of the appended claims and their equivalents.

The invention claimed is:

1. A method of scavenging free radicals in a mammal comprising: administering to the mammal an oral dosage form comprising alpha-lipoic acid, n-acetyl cysteine, green tea extract, turmeric extract, and quercetin and administering to the mammal a topical dosage form comprising bearberry extract, bitter orange peel extract, lemon extract, cucumber extract, acerola concentrate, asparagus stem extract, asparagus root extract and black cohosh extract.

2. The method of claim 1 wherein the oral dosage form is selected from the group consisting of a pill, capsule, gelcap, geltab, beverage, chewing gum, chewable tablet, lozenge, viscous gel, troche, toothpaste, gargling gel, mouth rinse, and combinations thereof.

3. The method of claim 1, wherein the topical dosage form is selected from the group consisting of an emulsion, solution, dispersion, gel, soap, transdermal patch, and combinations thereof.

4. The method of claim 1, wherein the topical dosage form is a lotion.

5. The method of claim 1, wherein each of the administering of the oral dosage form and the administering of the topical dosage form is repeated at least twice daily.

6. The method of claim 1, wherein the alpha-lipoic acid is present in the oral dosage form in an amount ranging from approximately 5-25 mg; the n-acetyl cysteine is present in the oral dosage form in an amount ranging from approximately 150-250 mg; the green tea extract is present in the oral dosage form in an amount ranging from approximately 50-100 mg; the turmeric extract is present in the oral dosage form in an amount ranging from approximately 5-50 mg; and the quercetin is present in the oral dosage form in an amount ranging from approximately 5-50 mg.

7. The method of claim 1, wherein the topical dosage form comprises approximately 0.5-5% of bearberry extract by weight; approximately 0.025-0.5% of bitter orange peel extract by weight; approximately 0.025-5% of lemon extract by weight; approximately 0.025-5% of cucumber extract by weight; approximately 0.025-5% of acerola concentrate by weight; approximately 0.25-2% of asparagus stem extract by weight; approximately 0.25-2% of asparagus root extract by weight; and approximately 0.25-2% of black cohosh extract by weight.

8. A method of reducing skin damage caused by ultraviolet radiation comprising administering to a mammal an oral dosage form comprising alpha-lipoic acid, n-acetyl cysteine, green tea extract, turmeric extract, and quercetin, and administering to the mammal a topical dosage form comprising bearberry extract, bitter orange peel extract, lemon extract, cucumber extract, acerola concentrate, asparagus stem extract, asparagus root extract and black cohosh extract.

9. The method of claim 8, wherein the oral dosage form is selected from the group consisting of a pill, capsule, gelcap, geltab, beverage, chewing gum, chewable tablet, lozenge, viscous gel, troche, toothpaste, gargling gel, mouth rinse, and combinations thereof.

10. The method of claim 8, wherein the topical dosage form is selected from the group consisting of an emulsion, solution, dispersion, gel, soap, transdermal patch, and combinations thereof.

11. The method of claim 8, wherein the topical dosage form is a lotion.

12. The method of claim 8, wherein each of the administering of the oral dosage form and the administering of the topical dosage form is repeated at least twice daily.

13. The method of claim 8, wherein the alpha-lipoic acid is present in the oral dosage form in an amount ranging from approximately 5-25 mg; the n-acetyl cysteine is present in the oral dosage form in an amount ranging from approximately 150-250 mg; the green tea extract is present in the oral dosage form in an amount ranging from approximately 50-100 mg; the turmeric extract is present in the oral dosage form in an amount ranging from approximately 5-50 mg; and the quercetin is present in the oral dosage form in an amount ranging from approximately 5-50 mg.

14. The method of claim 8, wherein the topical dosage form comprises approximately 0.5-5% of bearberry extract by weight; approximately 0.025-0.5% of bitter orange peel extract by weight; approximately 0.025-0.5% of lemon extract by weight; approximately 0.025-0.5% of cucumber extract by weight; approximately 0.025-0.5% of acerola concentrate by weight; approximately 0.25-2% of asparagus stem extract by weight; approximately 0.25-2% of asparagus root extract by weight; and approximately 0.25-2% of black cohosh extract by weight.

\* \* \* \* \*